United States Patent [19]

Kabis

[11] Patent Number: 5,686,673
[45] Date of Patent: Nov. 11, 1997

[54] SAMPLER

[76] Inventor: Thomas W. Kabis, P.O. Box 86, Solana Beach, Calif. 92075

[21] Appl. No.: 683,641

[22] Filed: Jul. 15, 1996

[51] Int. Cl.$^6$ ........................................ G01N 1/12
[52] U.S. Cl. ........................ 73/863.31; 73/864.51; 73/864.61
[58] Field of Search .............. 73/863.31, 864.31, 73/864.63–864.67, 867.61, 864.62, 864.51–864.53

[56] References Cited

U.S. PATENT DOCUMENTS

| | | | |
|---|---|---|---|
| 4,050,315 | 9/1977 | Markfelt | 73/864.66 |
| 4,078,433 | 3/1978 | McCabe, Jr. et al. | |
| 4,852,413 | 8/1989 | Niskin et al. | 73/864.63 |
| 4,949,582 | 8/1990 | Vollweiler | 73/864.63 |
| 5,454,275 | 10/1995 | Kabis | 73/864.51 |
| 5,471,886 | 12/1995 | Kalidindi | 73/864.63 |

FOREIGN PATENT DOCUMENTS

| | | | |
|---|---|---|---|
| 11336 | 2/1981 | Japan. | |
| 0900155 | 1/1982 | U.S.S.R. | 73/864.66 |
| 1272151 | 11/1986 | U.S.S.R. | |
| 1318833 | 6/1987 | U.S.S.R. | |
| 1328723 | 8/1987 | U.S.S.R. | 73/864.66 |

OTHER PUBLICATIONS

Dempsey et al., "Storage Hopper Sampling Device," IBM Technical Disclosure Bulletin, vol. 21, No. 11, pp. 4369–4370, Apr. 1979.
Mitchell et al., "Continuous Leak Water Sampler," AEC Research and Development Report, Union Carbide Nuclear Co., No. KY–423, pp. 1–3, Nov. 30, 1962.

*Primary Examiner*—Robert Raevis
*Attorney, Agent, or Firm*—Nydegger & Associates

[57] ABSTRACT

A sampler for simultaneously collecting multiple fluid samples is provided. The sampler includes a cap, at least one chamber fastener securing two sample chambers to the cap and an inlet providing substantially simultaneous flow into the sample chambers. The sampler can include a housing connected to the cap for enclosing the sample chambers and a housing seal which seals an interface formed between the housing and the cap. Inlet seals can be used to selectively seal the inlet to allow the sampler to collect accurate samples at a predetermined depth or below a free floating layer of fluid.

20 Claims, 3 Drawing Sheets

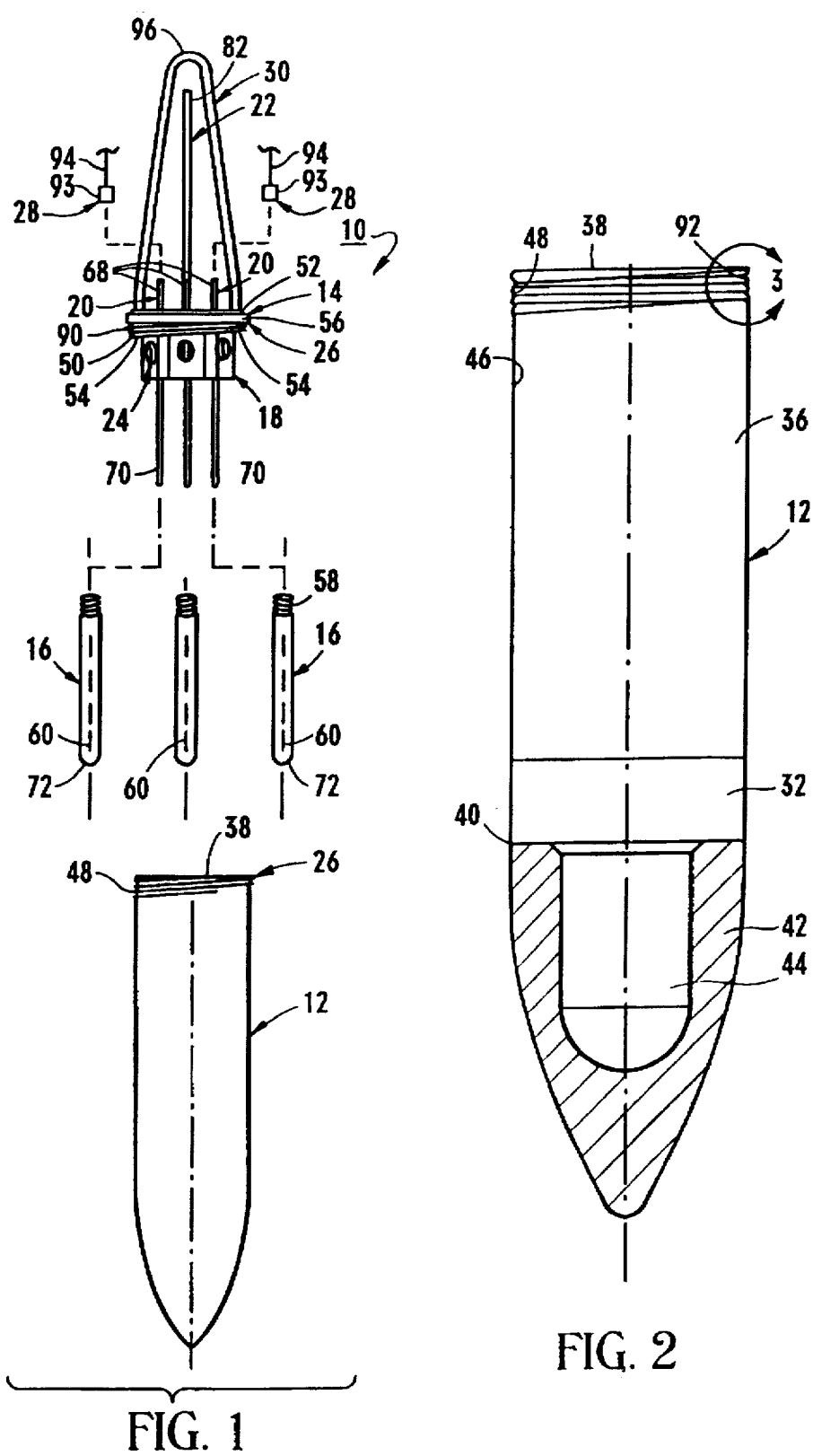

SAMPLER

FIELD OF THE INVENTION

The present invention relates to an improved sampler useful for collecting samples from fluids such as groundwater and beverages. The improved sampler is particularly, but not exclusively, useful for simultaneously collecting multiple samples from substantially the same location, collecting accurate samples from a predetermined depth and automated sampling systems.

BACKGROUND OF THE INVENTION

Samplers are commonly used to collect samples from a fluid supply to determine the overall composition of the fluid supply or the composition of the fluid supply at a particular level. For example, samples are commonly taken from groundwater to test for a number of organic and inorganic compounds such as gasoline, arsenic, chromium and nickel. These compounds can present a serious threat to public health and safety. The accurate detection of these compounds in the groundwater is instrumental in determining whether the groundwater is safe, what compounds are present in the groundwater and what measures are needed to remove the compounds from the groundwater.

Presently, many laboratories require testing upon three discrete samples, taken from the same location, for quality control reasons and to provide alternate samples for testing in the event that the integrity of one or two of the samples is compromised.

Samplers are currently available to acquire a single sample from a fluid supply. However, these samplers are not entirely satisfactory since, the sampler must be placed into the fluid supply multiple times to acquire multiple samples. During this time, the composition of the fluid supply can vary or the sample may not be collected from the same level. Thus, the multiple samples may not be consistent.

Further, if stratification exists in the fluid supply, it is important to collect accurate samples from different levels of the fluid supply to determine the composition of the fluid supply at the various levels. Similarly, if a layer of free floating fluid exists over the fluid supply, it is important to collect accurate samples of the fluid supply below the free floating fluid.

Many existing samplers begin filling with sample when the sampler is placed in the fluid supply. These samplers are unable to acquire an accurate sample from a predetermined level or below a free floating fluid.

Many existing samplers are not easily operated by automated robotics systems since these samplers are difficult to handle and removal of the sample from the sampler is difficult. Automated sampling systems utilizing robotics are needed to acquire samples at predetermined time intervals or from hazardous environments such as nuclear test sites.

In light of the above, it is an object of the present invention to provide a sampler with the ability to obtain multiple samples from substantially the same level and at substantially the same time. Another object of the present invention is to provide a sampler which accurately collects samples from a predetermined depth or below a layer of free floating fluid. Yet another object of the present invention is to provide a sampler which can be used with automated robotics systems for acquiring samples at predetermined time intervals or use in hazardous environments.

SUMMARY OF THE INVENTION

The present invention is directed to a sampler which satisfies these objectives. The sampler provided herein is suitable for simultaneously collecting at least two discrete samples from substantially the same location, is able to collect accurate samples from a predetermined depth or below a layer of free floating fluid and is suited for use with automated robotics systems.

A sampler for collecting a sample in at least two distinct sample chambers having features of the present invention includes a cap, at least one chamber fastener and an inlet. The cap includes a bottom and the chamber fastener is secured to the bottom of the cap. At least two distinct the sample chambers can be secured to the cap with the chamber fastener.

The inlet is in fluid communication with the sample chambers and allows for substantially simultaneous flow of the fluid sample into the distinct sample chambers when the sample chambers are secured to the chamber fastener. Since the inlet allows for substantially simultaneous flow into two separate sample chambers, the sampler is able to simultaneously obtain two separate and distinct samples from the same area.

Preferably, the sampler includes at least three sample chambers and each sample chamber is secured to the bottom of the cap with one chamber fastener. This allows the sampler to collect three fluid samples substantially simultaneously.

The inlet can be inlet tubes which extend through the cap. Each inlet tube including an upper inlet end which extends above a top of the cap, an inlet opening having an inlet cross-sectional area and a lower inlet end in fluid communication with one of the sample chambers.

Additionally, the sampler can include an exhaust which vents the sample chambers. The exhaust can be an exhaust tube having an upper exhaust end which extends above the top of the cap and an exhaust opening having an exhaust cross-sectional area.

Typically, the upper exhaust end extends farther above the top of the cap than does the upper inlet end of each inlet tube and the combined inlet cross-sectional areas of the inlet openings are substantially equal to the exhaust cross-sectional area of the exhaust opening. This allows for filling of the sample chambers through the inlet tubes since the pressure at the inlet openings is greater than the pressure at the exhaust opening.

Preferably, the sampler includes a housing which cooperates with the cap to enclose and protect the sample chambers. The housing can include a substantially tubular body having an open first end and a housing weight attached to an opposed second end. The housing can also be a container for retaining overflow sample from the sampler.

The sampler can also include a substantially rigid attacher to facilitate the handling of the sampler by a robot and to facilitate the retrieval of a lost or free floating sampler. The attacher extends upwardly from the top of the cap and is fixedly and rigidly secured to the top of the cap. Typically, the attacher has a distal end which extends above the upper inlet ends and the upper exhaust end to protect the inlet and exhaust tubes during usage.

To allow the sampler to collect accurate fluid samples from a predetermined depth or below a free floating fluid layer, the sampler can also include inlet seals and a housing seal. The inlet seals selectively and substantially inhibit the flow of fluid into the inlet tubes while the housing seal substantially inhibits the flow of fluid at an interface formed between the housing and the cap.

It is important to recognize that a sampler in accordance with the present invention can collect multiple fluid samples from substantially the same level and at substantially the same time. Further, the sampler can accurately collect samples from a predetermined depth or below a layer of free floating fluid. Also, the sampler can be used with automated systems for acquiring samples at predetermined time intervals or in hazardous environments.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a front, plan, exploded view of a sampler having features of the present invention;

FIG. 2 is a cutaway view of a housing having features of the present invention containing a fluid sample;

DESCRIPTION

Figure 3:
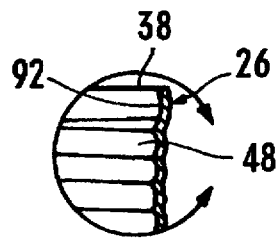
FIG. 3 is a cutaway view taken on line 3 in FIG. 2.

Referring initially to FIG. 1, a sampler 10 according to the present invention includes (i) a housing 12, (ii) a cap 14, (iii) a plurality of sample chambers 16, (iii) a plurality of chamber fasteners 18, (iv) an inlet 20, (v) an exhaust 22, (vi) a plurality overflow ports 24, (vii) a container seal 26, (viii) a plurality of inlet seals 28 and (ix) an attacher 30. As described in detail below, the sampler 10 is useful for collecting a fluid sample 32 in multiple, separate and distinct sample chambers 16 from a fluid supply 34.

The housing 12 protects the sample chambers 16 and preferably, retains any fluid sample 32 which overflows from the sample chambers 16 to collect an additional, separate fluid sample 32 for testing. As shown in FIG. 2, the housing 12 can include a substantially tubular body 36 having an open first end 38 and an opposed second end 40 and a housing weight 42 attached to the tubular body 36 at the second end 40. The housing weight 42 and the shape of the housing 12 enable the sampler 10 to sink substantially vertically in the fluid supply 34.

Figure 7:
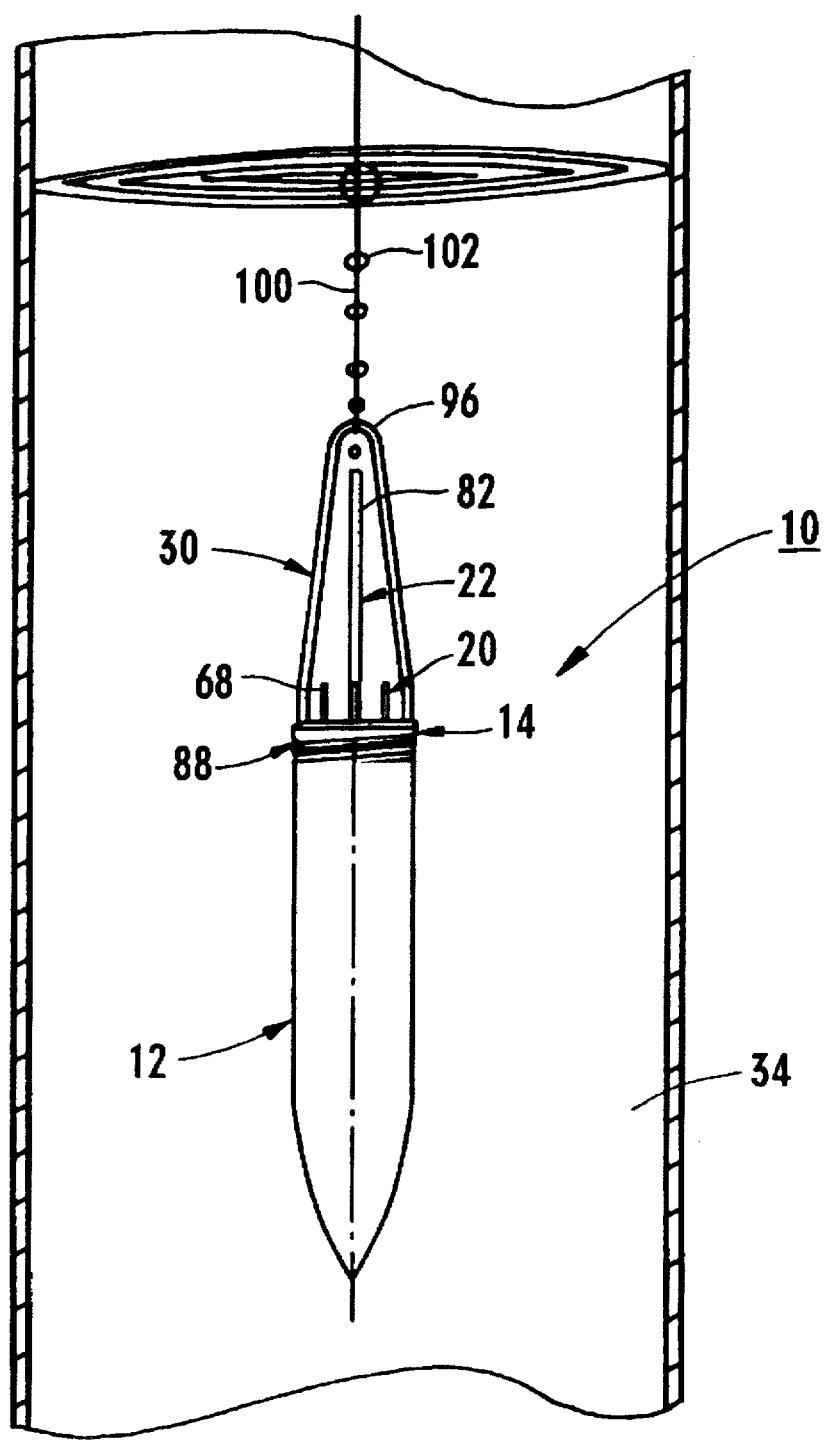
FIG. 7 is a front plan view of a sampler having features of the present invention disposed in a fluid supply.

In the embodiment shown in FIGS. 1, 2 and 7, the tubular body 36 is substantially annular and the housing weight 42 has a parabolic cross-sectional shape to facilitate smooth vertical movement of the sampler 10 through the fluid supply 34. In this embodiment, the tubular body 36 is about 8.4 inches in length, about 3.5 inches in diameter and has a wall thickness of about 0.03 inches, while the housing weight 42 is about 5.3 inches long. As shown in FIG. 2, the housing weight 42 can include a hollow, central portion 44.

However, in alternate versions of the present invention, the tubular body 36 and/or housing weight 42 could have an alternate cross-sectional shape, length or width.

Typically, the tubular body 36 and the housing weight 42 can be machined as an integral unit for ease of manufacturing. Alternately, the tubular body 36 and housing weight 42 can be two separate pieces which are welded or adhered together.

The cap 14 is selectively secured to the housing 12 proximate the open first end 38 of the tubular body 36 and substantially encloses the open first end 38. The cap 14 can be secured to the tubular body 36 in a number of alternate ways. For example, an interior surface 46 of the tubular body can include a housing fastener 48, i.e., an internally threaded surface proximate the open first end 38 of the tubular body and the cap 14 can include a corresponding and mating cap fastener 50, i.e., an externally threaded surface. In this embodiment, the internally threaded surface and the externally threaded surface are about 3.5×8 threads. Alternately, the housing fastener 48 could include an externally threaded surface and the cap fastener 50 could include an internally threaded surface for selectively attaching the cap 14 to the housing 12.

The cap 14 retains the chamber fasteners 18, the inlet 20, the exhaust 22, and the attacher 30. As shown in the Figures, the cap 14 can be substantially right cylindrical shaped and have a top 52, a bottom 54, and a side surface 56. The cap fastener 50, i.e., the externally threaded surface discussed previously is disposed in the side surface 56 of the cap 14 proximate the bottom 54.

The sample chambers 16 receive and retain the fluid sample 32 for subsequent testing. Preferably, each sample chamber 16 is a sterile vial which can subsequently be used during analysis of the fluid sample 32. This is preferred since the fluid sample 32 does not have to be transferred to another container for analysis. Thus, there is less chance for contamination or error.

Each sample chamber 16 is preferably, selectively attached to the cap 14 so that the sample chamber 16 can be readily removed from the sampler 10 for testing. The selective attachment of the sample chambers 16 can be accomplished in a number of alternate ways. For example, as show in FIG. 1, each sample chamber 16 includes a chamber receiver 58, i.e., an externally threaded surface for attachment to one of the chamber fasteners 18 as detailed below. Alternately, each chamber receiver 58 can include an internally threaded surface (not shown) or some other means for attaching the sample chamber 16 to the chamber receivers 58.

Each of the sample chambers 16 shown in FIG. 1 is substantially hollow, cylindrical and shaped similar to a test tube. Each sample chamber includes a longitudinal axis 60. Each sample chamber is about 4.0 inches long and about 0.75 inches in diameter. In the embodiment shown in the Figures, the longitudinal axes 60 of the sample chambers 16 are substantially parallel when attached to the cap 14. Alternately, one or more of the sample chambers 16 could be disposed within a larger sample chamber (not shown) and the longitudinal axes of some of the sample chambers 16 could be substantially coaxial. However, this would complicate the installation and removal of the sample chambers 16 from the chamber fasteners 18.

The chamber fasteners 18 are secured to the bottom 54 of the cap 14. Typically, each chamber fastener 18 selectively attaches one of the sample chambers 16 to the cap 14 and the number of the chamber fasteners 18 is equal to the number of sample chambers 16. Alternately, a single, chamber fastener 18 could retain multiple sample chambers 16 or multiple chamber fasteners 18 could retain a single sample chamber 16.

Figure 5:
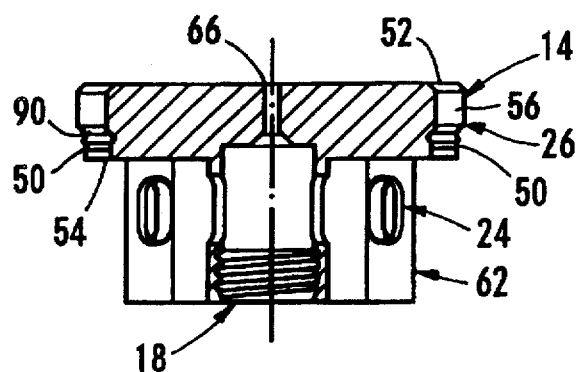
FIG. 5 is a front plan view, in partial cutaway of the cap of FIG. 4.
Figure 4:
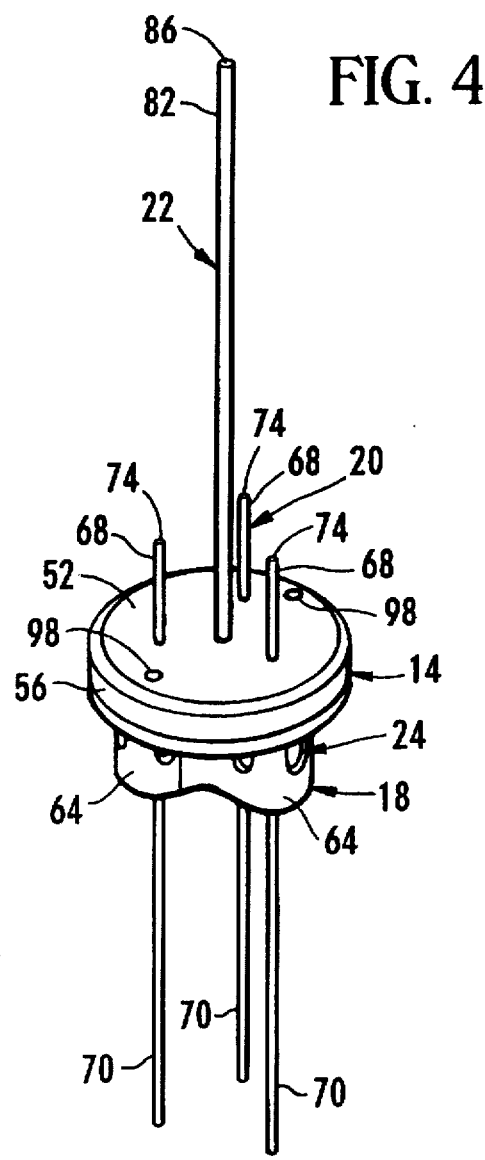
FIG. 4 is a perspective view of a cap, an inlet and an exhaust having features of the present invention.
Figure 6:
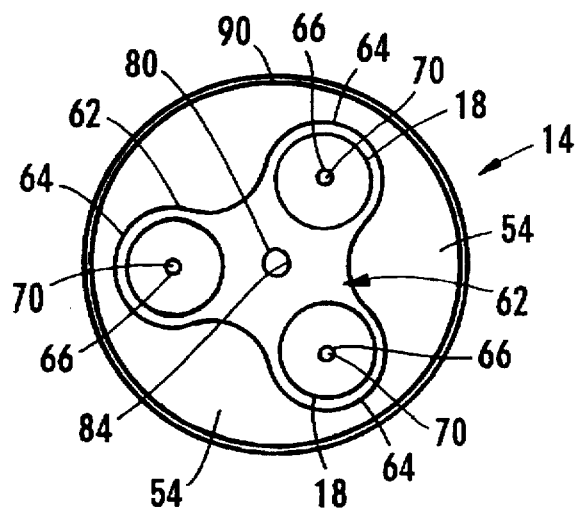
FIG. 6 is a bottom plan view of the cap, inlet and exhaust of FIG. 4.

The embodiment shown in the Figures includes three chamber fasteners 18. In this embodiment, as can best be viewed from FIGS. 4–6, the chamber fasteners 18 are disposed in a fastener projection 62 which extends downwardly from the bottom 54 of the cap 14. The fastener projection 62 includes a cross-section having three lobes 64. Each lobe 64 includes one chamber fastener 18, i.e. an internally threaded surface for selectively retaining one of the sample chambers 16.

Alternately, for example, each chamber fastener 18 could be an individual tubular projection (not shown) and/or each chamber fastener 18 could include an externally threaded surface (not shown).

For ease of manufacturing, the cap 14 and chamber fasteners 18 can be manufactured as an integral unit. Alternately, the chamber fasteners 18 can be welded or adhered to the cap 14 in a way that is know by those skilled in the art.

The inlet 20 is in fluid communication with the separate sample chambers 16 and allows for substantially simultaneous flow of the fluid sample 32 into the distinct sample chambers 16. Typically, the inlet 20 is a plurality of inlet tubes which extend through inlet cap apertures 66 in the cap 14. Alternately, a single inlet tube (not shown) could split and be in fluid communication with two or more sample chambers 16 or more than one inlet tube could extend through the cap 14 and be in fluid communication with a single sample chamber 16.

In the embodiment shown in the Figures, the inlet 20 includes three inlet tubes. Each inlet tube extends through the cap 14 into one sample chamber 16. Each inlet tube includes an upper inlet end 68 which extends above the top 52 of the cap 14 and a lower inlet end 70 which extends below the bottom 54 of the cap 14. The upper inlet end 68 extends about one inch above the top 52 of the cap 14. The lower inlet end 70 is disposed inside one of the sample chambers 16. Preferably, the lower inlet end 70 extends substantially to a chamber bottom 72 of each sample chamber 16 to ensure smooth flow of fluid sample 32 into the sample chamber 16.

Each inlet tube is annular and includes an inlet opening 74 for allowing flow of the fluid sample 32 through the inlet tube. In the embodiment shown in the Figures, each inlet tube has an inside diameter of about 0.125 inches. Accordingly, the inlet opening 74 has an inlet cross-sectional area of about 0.012 square inches to insure slow, smooth flow. Preferably, the inside diameter of each of the inlet tubes is substantially equal so that the separate sample chambers 16 fill at substantially the same rate. Alternatively, the inside diameter for each inlet tube can vary to allow for a different rate of flow into the separate sample chambers 16.

The exhaust 22 vents the sample chambers 16 and can extend through the cap 14. Preferably, the exhaust 22 also vents the housing 12 to allow for fluid sample 32 from the sample chambers 16 to overflow into the housing 12 as detailed above.

The exhaust 22 can be implemented in a number of alternate ways. For example, the exhaust 22 can be a single tube which extends through an exhaust cap aperture 80 in the cap 14. Alternately, the exhaust 22 can be a separate tube (not shown) for venting each sample chamber 16. However, this would increase the cost of manufacturing of the sampler 10.

In the embodiment shown in the Figures, the exhaust 22 is a single exhaust tube which includes an upper exhaust end 82 which extends about seven inches above the top 52 of the cap 14 and a lower exhaust end 84 which can extend below the bottom 54 of the cap 14. The exhaust tube is annular and includes an exhaust opening 86 for venting the sampler 10. In the embodiment shown in the Figures, the exhaust tube has an inside diameter of about 0.250 inches. Accordingly, the exhaust opening 86 has an exhaust cross-sectional area of about 0.05 square inches.

Fluid sample 32 flows into the inlet when the pressure at the inlet opening 74 is greater than the pressure at the exhaust opening 86. Since the density of the fluid sample 32 and gravity are substantially the same at the inlet opening 74 and the exhaust opening 86, the variables which determine whether a pressure differential exists between the inlet opening 74 and the exhaust opening 86 are the head, i.e., the distance below a liquid surface and the area of the opening.

In the embodiment shown in the Figures, a pressure differential exists since the upper exhaust end 82 extends farther above the top 52 of the cap 14 than does the upper inlet ends 68 and the combined inlet cross-sectional areas of the inlet openings 74 are substantially equal to the exhaust cross-sectional area of exhaust opening 86.

The overflow port 24 allows for fluid sample 32 from the sample chambers 16 to overflow into the housing 12. The overflow port 24 can be located in the cap 14, in each sample chamber 16 or in the chamber fasteners 18. In the embodiment shown in the figures, the overflow port 24 is an aperture in the chamber fasteners 18.

The housing seal 26 substantially seals an interface 88 formed between the cap 14 and the housing 12 and inhibits the flow of fluid at the interface 88. The housing seal 26 is particularly useful when fluid samples 32 are needed at a predetermined depth or below a free floating fluid layer to prevent unwanted flow into the sampler 10 which can adversely effect the integrity of the fluid sample 32.

Referring to FIG. 1, the housing seal 26 can comprise a beveled surface 90 disposed in the side surface 56 of the cap 14 and a circumferential ring 92 in the tubular body 36. The circumferential ring 92 is forced against the beveled surface 90 to obtain a substantially fluid-tight seal when the cap 14 is secured to housing 12. The beveled surface 90 is positioned between the cap fastener 50 and the top 52 of the cap 14. The circumferential ring 92 is positioned above the housing fastener 48.

The inlet seal 28 selectively encloses at least one of the inlets 20 in a substantially fluid tight fashion and substantially inhibits the flow of fluid into that inlet 20. The inlet seal 28 allow the sampler 10 to be lowered to a predetermined depth and lowered through a free floating fluid level without collecting fluid in the sample chambers 16. Thus, the sample chambers 16 do not fill until the sampler 10 reaches the desired predetermined depth.

The design of the inlet seal 28 varies according to the design of the inlet 20. In the embodiment shown in the FIG. 1, the inlet seal 28 is a tube sized to snugly fit over the upper inlet end 68 with an enclosed end 93 for sealing the inlet 20. Alternately, the inlet seal 28 could be a plug (not shown) sized to fit inside and seal each inlet opening 74.

A seal connector 94, i.e. string, chain, wire or fishing line can be attached to the inlet seal 28 to facilitate removal of the inlet seal 28 from the inlet tube when the sampler 10 reaches the desired depth. The inlet seals 28 can be removed at different depths to acquire fluid samples 32 from the different depths. For example one inlet seal 28 could be removed at a depth of ten feet while a second inlet seal 28 could be removed at a depth of twenty feet.

The attacher 30 is substantially rigid and is fixedly and rigidly secured to the top 52 of the cap. The attacher 30 extends upwardly away from the top 52 of the cap 14. Preferably, a distal end 96 of the attacher 30 extends at least as far above the top 52 as does the upper exhaust end 82 to protect the inlet 20 and exhaust 22. As shown in the Figures, the attacher 30 can be a solid, arched shaped bar which is secured to attacher cap apertures 98 in the top 10 of the cap.

A sampler connector 100 is connected to the attacher 30 for raising or lowering the sampler 10 in correct orientation, i.e., substantially vertical. Further, the attacher 30 provides a hook for retrieving the sampler 10 if the sampler connector 100 breaks and provides a support so that a robot (not shown) can be used to manipulate the sampler 10, remove the cap 14 and remove the sample chambers 16 in a hazardous environment.

The sample connector 100 can be a string, cord, chain, wire or fishing line which is raised and lowered manually or with a motor (not shown). Preferably, the sample connector 100 or the motor includes a monitoring device so that the rate in which the sampler 10 is lowered and raised into the fluid supply 34 can be monitored and/or controlled. For example, a scaled engineering tape having the distance printed thereon can be used in conjunction with a time piece to monitor the decent and accent of the sampler 10.

The rate at which the sampler 10 is raised or lowered varies according to the dimensions of the sampler 10 and the fluid supply 34. For groundwater with the sampler described above, a rate of about twenty feet per minute is adequate.

Optimally, the housing 12, the cap 14, the ports and the attacher 30 are made of stainless steel, since stainless steel is resistant to corrosion in harsh environments and can be readily cleaned or sterilized. An excellent sampler 10 can be made from 321 stainless steel. Alternately, depending on the composition of the fluid supply 34, portions of the sampler 10 can be made from plastic or some other material.

OPERATION

An example of the operation of a sampler 10 having features of the present invention can best be visualized with reference to FIGS. 1 and 7. The operation begins with the decontamination of the individual components of the sampler 10 with steam or some other method. Next, the sample chambers 16 are attached to the chamber fasteners 18. Subsequently, the cap 14 is attached to the tubular body 36. The cap 14 and tubular body 36 cooperate to substantially enclose and protect the sample chambers 16. The housing seal 26 substantially seals the interface 88 between the cap 14 and the housing 12 to inhibit fluid flow at this interface 88.

Next, the a hose (not shown) is connected to the upper exhaust end 82 of the exhaust 22. Dry nitrogen gas (not shown) is then released into the sampler 10 through the hose for thirty or forty seconds to purge the sampler 10.

After purging is complete, the hose is removed, and the sampler connector 100 is attached to the attacher 30 for lowering the sampler 10 into the fluid supply 34.

Inlet seals 28 can be attached to the inlet 20 to inhibit the flow of fluid into the sample chambers 16 until the sampler 10 is lowered to the desired depth. When the sampler 10 is lowered to the predetermined depth, the seal connectors 94 are pulled, thereby removing the inlet seals 28. Since the upper inlet ends 68 are lower than the upper exhaust end 82 and the combined inlet cross-sectional area of the inlet openings 74 is about the same as that of the exhaust cross-sectional area of the exhaust opening 86, the fluid sample 32 begins to flow into the sample chambers 16 and the gas 102 in the sampler 10 begins to vent through the exhaust 22.

Since the inlet tubes are small and extend into the sample chambers 16, the sample chambers 16 fill gradually with little disruptive fluid flow.

After the sampler 10 has been retained at the required depth for a sufficient time the sampler 10 is raised to the surface. The required time to fill the sample chambers 16 varies according to the fluid supply 34 and the sizing of the components of the sampler 10. For example, for the sampler 10 described above, about six minutes is sufficient in water.

Upon reaching the surface, the cap 14 is removed from the housing 12 and the sample chambers 16 are removed from the chamber fasteners 18. The sample chambers 16 are then sealed and sent to the laboratory for testing. Additionally, any fluid sample 32 which overflows through the overflow ports 24 into the housing 12 can be transferred into a testing container.

Next, the sampler is decontaminated and the entire process is repeated.

While the particular sampler 10 as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A sampler for substantially simultaneously collecting a fluid sample in at least two distinct sample chambers, the sampler comprising:
   (a) a cap having a bottom;
   (b) at least one chamber fastener secured to the bottom of the cap for securing at least two of the distinct sample chambers to the cap; and
   (c) an inlet in fluid communication with the sample chambers and allowing for substantially simultaneous flow of the fluid sample into the distinct sample chambers when the sample chambers are secured to the chamber fastener.

2. The sampler of claim 1 comprising at least two chamber fasteners secured to the bottom of the cap and at least two sample chambers, wherein, each chamber fastener selectively retains one of the sample chambers to the cap.

3. The sampler of claim 2 wherein each of the sample chambers is substantially tubular and includes a longitudinal axis and the longitudinal axes of at least two of the sample chambers are substantially parallel when secured to the chamber fasteners.

4. The sampler of claim 1 comprising at least three chamber fasteners secured to the bottom of the cap and at least three sample chambers, wherein, each chamber fastener selectively secures one of the sample chambers to the cap.

5. The sampler of claim 1 wherein the inlet comprises at least two inlet tubes which extend through the cap, each inlet tube including an upper inlet end which extends above a top of the cap and a lower inlet end which is in fluid communication with one of the sample chambers when the sample chambers are secured to the chamber fastener, and the sampler comprises an exhaust tube which vents the sample chambers, the exhaust tube having an upper exhaust end which extends farther above the top of the cap than does the upper inlet end of each inlet tube.

6. The sampler of claim 5 wherein each inlet tube has an inlet opening with an inlet cross-sectional area and the exhaust tube has an exhaust opening with an exhaust cross-sectional area, wherein, the combined inlet cross-sectional areas of the inlet openings are substantially equal to the exhaust cross-sectional area of the exhaust opening.

7. The sampler of claim 5 comprising a substantially rigid attacher for attachment to a sampler connector for raising and lowering the sampler, the attacher is substantially, rigidly secured to the top of the cap, the attacher includes a distal end which extends above the top of the cap at least as far as the upper exhaust end.

8. The sampler of claim 1 comprising a housing selectively secured to the cap, the housing and cap cooperating to substantially enclose the sample chambers when the sample chambers are secured to the chamber fastener and a housing seal for substantially inhibiting the flow of fluid sample at an interface formed between the housing and the cap.

9. The sampler of claim 8 wherein (i) the chamber fastener includes at least one overflow port which allows for the overflow of fluid sample when at least one of the sample chambers is substantially filled with fluid sample and (ii) the housing is suitable for retaining the overflow of fluid sample.

10. The sampler of claim 1 comprising an inlet seal for selectively and substantially inhibiting the flow of fluid sample into at least one of the distinct sample chambers.

11. A sampler for collecting a fluid sample in at least one sample chamber, the sampler comprising:
  (a) a housing suitable for receiving a fluid sample, the housing including a substantially tubular body having an open first end and an opposed second end and a housing weight attached proximate to the second end of the tubular body, the tubular body also having a housing internally threaded surface proximate the first end and a circumferential ring positioned above the internally threaded surface;
  (b) a cap selectively attached to the housing which substantially encloses the open first end, the cap having a top, a bottom, and a side surface having an externally threaded surface proximate the bottom of the cap which corresponds with and mates with the housing internally threaded surface to selectively secure the cap to the housing, the side surface also having a beveled surface disposed between the externally threaded surface and the top of the cap;
  (c) at least one chamber fastener secured to the bottom of the cap for securing at least one sample chamber to the cap;
  (d) at least one inlet tube extending through the top and bottom of the cap, each inlet tube including an upper inlet end which extends above the top of the cap and a lower inlet end in fluid communication with one sample chamber, when the sample chamber is secured to the chamber fastener;
  (e) an exhaust tube which vents at least one sample chamber when the sample chamber is secured to the chamber fastener, the exhaust tube having an upper exhaust end which extends above the top of cap; and
  (f) a housing seal formed by the interaction between the circumferential ring and the beveled surface for substantially inhibiting the flow of fluid sample at an interface formed between the tubular body and the cap.

12. The sampler of claim 11 comprising an inlet seal for selectively and substantially inhibiting the flow of fluid sample into at least one inlet tube.

13. A sampler for collecting a fluid sample in at least two sample chambers, the sampler comprising:
  (a) a housing suitable for receiving a fluid sample, the housing including a substantially tubular body having an open first end and an opposed second end and a weight attached proximate to the second end of the tubular body;
  (b) a cap selectively attached to the housing which substantially encloses the open first end, the cap having a top and a bottom;
  (c) at least one chamber fastener secured to the bottom of the cap for securing at least one sample chamber to the cap;
  (d) a plurality of inlet tubes extending through the top and bottom of the cap, each inlet tube including an upper inlet end and a lower inlet end in fluid communication with one of the sample chambers, when the sample chambers are secured to the chamber fastener;
  (e) an exhaust tube which vents at least one of the sample chambers when the sample chambers are secured to the chamber fastener; and
  (f) a plurality of inlet seals, each inlet seal for selectively and substantially inhibiting the flow of fluid sample at the upper inlet end of one inlet tube.

14. The sampler of claim 13 wherein each inlet seal comprises a tube having an enclosed end which encloses the upper inlet end of one of the inlet tubes and a seal connector which connects to the enclosed end to allow for the inlet seal to be selectively removed from the inlet tube.

15. A sampler comprising:
  (a) a housing suitable for receiving a fluid sample, the housing including a substantially tubular body having a housing internally threaded surface disposed proximate an open, first end of the tubular body and a housing weight attached proximate to an opposed second end of the tubular body;
  (b) a cap having (i) a top, (ii) a bottom, and (iii) a side surface including a cap externally threaded surface which corresponds with and mates with the housing internally threaded surface to selectively secure the cap to the housing;
  (c) three sample chambers suitable for receiving a fluid, each sample chamber including a chamber externally threaded surface;
  (d) three chamber fasteners secured to the bottom of the cap, each chamber fastener including a fastener internally threaded surface which corresponds with and mates with chamber externally threaded surface for selectively securing one of the sample chambers to the cap;
  (e) three inlet tubes extending through the top and bottom of the cap, each inlet tube being in fluid communication with one of the sample chambers;
  (f) an exhaust tube extending through the top and bottom of the cap, the exhaust tube venting the housing and the three sample chambers;
  (g) a overflow port allowing for the transfer of fluid from at least one of the sample chambers to the housing; and
  (h) a housing seal for substantially inhibiting the flow of fluid sample at an interface formed between the cap and the tubular housing.

16. A sampler for collecting a fluid sample in at least two distinct sample chambers, the sampler comprising:
  (a) a cap having a bottom;
  (b) at least one chamber fastener secured to the bottom of the cap for securing at least two of the distinct sample chambers to the cap;
  (c) at least two inlet tubes which extend through the cap, each inlet tube including a lower inlet end which is in fluid communication with one of the sample chambers when the sample chambers are secured to the chamber fastener; and (d) an exhaust tube which vents the sample chambers.

17. The sampler of claim 16 comprising a total of at least two chamber fasteners secured to the bottom of the cap, wherein, each chamber fastened selectively retains one (1) of the sample chambers to the cap.

18. The sampler of claim 16 wherein each inlet tube has an upper inlet end which extends above a top of the cap and an inlet opening with an inlet cross-sectional area and the exhaust tube has an upper exhaust end which extends farther above the top of the cap than does the upper inlet end of each inlet tube and an exhaust opening with an exhaust cross-sectional area, wherein, the combined inlet cross-sectional areas of the inlet openings are substantially equal to the exhaust cross-sectional area of the exhaust opening.

19. The sampler of claim 18 comprising a substantially rigid, attacher suitable for attachment to a sampler connector for raising and lowering the sampler, the attacher being substantially, rigidly secured to a top of the cap, the attacher having a distal end which extends above the top of the cap, wherein, the distal end of the attacher extends at least as far above the top of the cap as does the upper exhaust end.

20. The sampler of claim 16 comprising at least two inlet seals, each inlet seal for selectively and substantially inhibiting the flow of fluid sample into one of the distinct sample chambers.

* * * * *